United States Patent
Beard et al.

(10) Patent No.: US 8,846,760 B2
(45) Date of Patent: Sep. 30, 2014

(54) DIHYDRONAPHTHALENE AND NAPHTHALENE DERIVATIVES AS N-FORMYL PEPTIDE RECEPTOR LIKE-1 (FPRL-1) RECEPTOR MODULATORS

(71) Applicant: Allergan, Inc., Irvine, CA (US)

(72) Inventors: Richard L. Beard, Newport Beach, CA (US); Vidyasagar Vuligonda, Irvine, CA (US); John E. Donello, Dana Point, CA (US); Veena Viswanath, Irvine, CA (US); Michael E. Garst, Newport Beach, CA (US); Thong Vu, Garden Grove, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/148,377

(22) Filed: Jan. 6, 2014

(65) Prior Publication Data

US 2014/0128471 A1    May 8, 2014

Related U.S. Application Data

(62) Division of application No. 13/409,228, filed on Mar. 1, 2012, now Pat. No. 8,653,299.

(60) Provisional application No. 61/453,827, filed on Mar. 17, 2011.

(51) Int. Cl.
| | | |
|---|---|---|
| *A61K 31/195* | (2006.01) | |
| *A61K 31/16* | (2006.01) | |
| *C07C 235/82* | (2006.01) | |
| *C07C 235/84* | (2006.01) | |
| *C07C 233/59* | (2006.01) | |

(52) U.S. Cl.
CPC ............ *C07C 235/84* (2013.01); *C07C 235/82* (2013.01); *C07C 2102/10* (2013.01); *C07C 233/59* (2013.01)
USPC ............ 514/563; 514/617; 562/457; 564/180

(58) Field of Classification Search
CPC .... A61K 31/195; A61K 31/16; C07C 235/82; C07C 233/59
USPC .................... 514/195, 617; 562/457; 564/180
See application file for complete search history.

(56) References Cited

U.S. PATENT DOCUMENTS

| 5,128,470 | A | 7/1992 | Klaus | |
|---|---|---|---|---|
| 7,931,909 | B2 | 4/2011 | Hughes | |
| 8,785,456 | B2 * | 7/2014 | Ren et al. | 514/263.22 |
| 2007/0117840 | A1 * | 5/2007 | Itoh et al. | 514/309 |
| 2010/0035932 | A1 | 2/2010 | Schepetkin | |
| 2011/0301179 | A1 | 12/2011 | Xiao et al. | |

FOREIGN PATENT DOCUMENTS

| EP | 1652837 | 3/2006 |
|---|---|---|
| EP | 2143714 | 1/2011 |
| WO | 2010-048302 | 4/2010 |

OTHER PUBLICATIONS

Cross, L.C. et al, Rules For the Nomenclature of Organic Chemistry, Section E: Stereochemistry, Pure & Appl. Chem., 1976, 11-30, 45.
Heinrich Stahl, Pharmaceutical Salts, Handbook of Pharmaceutical Salts, 2002, 329-345, International Union of Pure and Applied Chemistry, Verlag Helvetica Chemica Acta—Zürich.
Migeotte, Isabelle et al., Formyl peptide receptors: A promiscuous subfamily of G protein-coupled receptors controlling immune responses, Cytokine & Growth Factor Reviews, 2006, 501-519, 17, US.
Perretti, Mauro et al, Therapeutic Anti-Inflammatory Potential of Formyl-Peptide Receptor Agonists, Pharmacology & Research, 2010, 175-188, 127.
Talavdekar, R.V. et al, Azoic Dyes. Part X. Brominated Naphthols, Proceedings of the Indian Academy of Sciences, Jul. 6, 1950, 292-303.
Tsuruki, Takahiro et al., Orally administered FPRL1 receptor agonist peptide MMK-1 inhibits etoposide-induced alopecia by a mechanism different from intraperitoneally administered MMK-1, Peptides, 2006, 820-825, 27, US.
Tripathy et al., Agricultural and Biological Chemistry, 1973, 37(6), 1375-1383.
Liu et al., Chinese Journal of Chemistry, 857-864, 2005.
West, Anthony R., Solid State Chemistry and its Applications, Wiley, New York, 1988, pp. 358 & 365.
Patent Cooperation Treaty, Notification of Transmittal of the International Search Report and the Written Opinion of the International Searching Authority, or the Declaration, Form PCTIISN220, Int. App. No. PCT/US2012/027419, Jun. 25, 2012.

\* cited by examiner

*Primary Examiner* — Shailendra Kumar
(74) *Attorney, Agent, or Firm* — Doina G. Ene

(57) ABSTRACT

The present invention relates to novel dihydronaphthalene and naphthalene derivatives, processes for preparing them, pharmaceutical compositions containing them and their use as pharmaceuticals as modulators of the N-formyl peptide receptor like-1 (FPRL-1) receptor.

8 Claims, No Drawings

DIHYDRONAPHTHALENE AND NAPHTHALENE DERIVATIVES AS N-FORMYL PEPTIDE RECEPTOR LIKE-1 (FPRL-1) RECEPTOR MODULATORS

RELATED APPLICATION

This application is a divisional application of U.S. Non-Provisional patent application Ser. No. 13/409,228, filed Mar. 1, 2012, now U.S. Pat. No. 8,653,299 which claims the benefit of U.S. Provisional Patent Application Ser. No. 61/453,827, filed Mar. 17, 2011, all of which are incorporated here by reference in their entirety.

FIELD OF THE INVENTION

The present invention relates to novel dihydronaphthalene and naphthalene derivatives, processes for preparing them, pharmaceutical compositions containing them and their use as pharmaceuticals as modulators of the N-formyl peptide receptor like-1 (FPRL-1) receptor. The invention relates specifically to the use of these compounds and their pharmaceutical compositions to treat disorders associated with the N-formyl peptide receptor like-1 (FPRL-1) receptor modulation.

BACKGROUND OF THE INVENTION

The N-formyl peptide receptor like-1 (FPRL-1) receptor is a G protein-coupled receptor that is expressed on inflammatory cells such as monocytes and neutrophils, as well as T cells and has been shown to play a critical role in leukocyte trafficking during inflammation and human pathology. FPRL-1 is an exceptionally promiscuous receptor that responds to a large array of exogenous and endogenous ligands, including Serum amyloid A (SAA), chemokine variant sCKβ8-1, the neuroprotective human peptide, anti-inflammatory eicosanoid lipoxin A4 (LXA4) and glucocorticoid-modulated protein annexin A1. FPRL-1 transduces anti-inflammatory effects of LXA4 in many systems, but it also can mediate the pro-inflammatory signaling cascade of peptides such as SAA. The ability of the receptor to mediate two opposite effects is proposed to be a result of different receptor domains used by different agonists (Parmentier, Marc et al. Cytokine & Growth Factor Reviews 17 (2006) 501-519).

Activation of FPRL-1 by LXA4 or its analogs and by Annexin I protein has been shown to result in anti-inflammatory activity by promoting active resolution of inflammation which involves inhibition of polymorphonuclear neutrophil (PMN) and eosinophil migration and also stimulate monocyte migration enabling clearance of apoptotic cells from the site of inflammation in a nonphlogistic manner. In addition, FPRL-1 has been shown to inhibit natural killer (NK) cell cytotoxicity and promote activation of T cells which further contributes to down regulation of tissue damaging inflammatory signals. FPRL-1/LXA4 interaction has been shown to be beneficial in experimental models of ischemia reperfusion, angiogenesis, dermal inflammation, chemotherapy-induced alopecia, ocular inflammation such as endotoxin-induced uveitis, corneal wound healing, re-epithelialization etc. FPRL-1 thus represents an important novel pro-resolutionary molecular target for the development of new therapeutic agents in diseases with excessive inflammatory responses.

SUMMARY OF THE INVENTION

A group of novel compounds which are potent and selective FPRL-1 modulators has been discovered. As such, the compounds described herein are useful in treating a wide variety of disorders associated with modulation of FPRL-1 receptor. The term "modulator" as used herein, includes but is not limited to: receptor agonist, antagonist, inverse agonist, inverse antagonist, partial agonist, partial antagonist.

This invention describes compounds of Formula I, which have FPRL-1 receptor biological activity. The compounds in accordance with the present invention are thus of use in medicine, for example in the treatment of humans with diseases and conditions that are alleviated by FPRL-1 modulation.

In one aspect, the invention provides a compound having Formula I or the geometrical isomers, enantiomers, diastereoisomers, tautomers, zwitterions and pharmaceutically acceptable salts thereof:

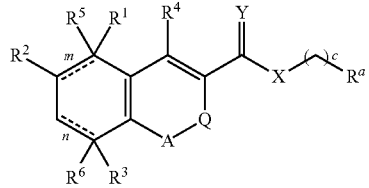

Formula I wherein:

" $\overset{m}{\text{-----}}$ " is a single bond or a double bond;

" $\overset{n}{\text{-----}}$ " is a single bond or a double bond;

$R^1$ is H, halogen, —S(O)$R^{10}$, —S(O)$_2R^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, NR$^{13}$R$^{14}$, C$_{3-8}$ cycloalkyl, C$_{3-8}$ cycloalkenyl or hydroxyl;

$R^2$ is H, halogen, —S(O)$R^{10}$, —S(O)$_2R^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, NR$^{13}$R$^{14}$, C$_{3-8}$ cycloalkyl, C$_{3-8}$ cycloalkenyl or hydroxyl;

$R^3$ is H, halogen, —S(O)$R^{10}$, —S(O)$_2R^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)$R^{12}$, NR$^{13}$R$^{14}$, C$_{3-8}$ cycloalkyl, C$_{3-8}$ cycloalkenyl, C$_{6-10}$ aryl or hydroxyl;

$R^4$ is H or C(O)$R^{12}$;

$R^5$ is H, —OC$_{1-6}$ alkyl, —SC$_{1-6}$ alkyl, —C$_{1-6}$ alkyl, —C$_{2-6}$ alkenyl or —C$_{2-6}$ alkynyl;

$R^6$ is H, —OC$_{1-6}$ alkyl, —SC$_{1-6}$ alkyl, —C$_{1-6}$ alkyl, —C$_{2-6}$ alkenyl or —C$_{2-6}$ alkynyl;

Y is O or S;

X is O, NR, or CH$_2$;

$R^a$ is C$_{6-10}$ aryl,

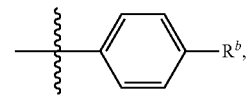

heteroaryl, C$_{3-8}$ cycloalkyl, C$_{3-8}$ cycloalkenyl or H;

$R^b$ is halogen;

c is 0, 1 or 2;

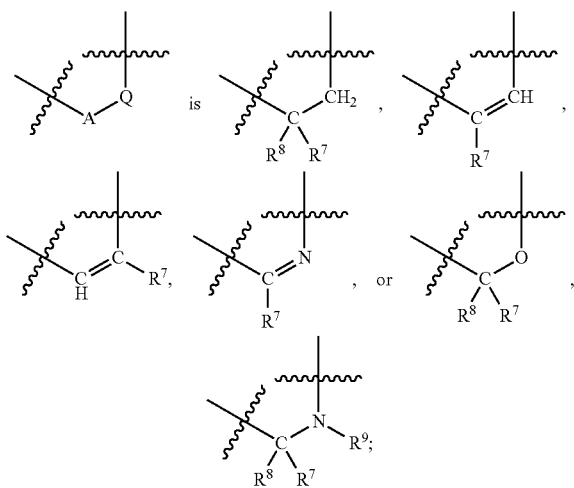

R[7] is H, halogen, —S(O)R[10], —S(O)$_2$R[11], nitro, hydroxyl, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)R[12], NR[13]R[14], C$_{3-8}$ cycloalkenyl or C$_{3-8}$ cycloalkyl;

R[8] is H, halogen, —S(O)R[10], —S(O)$_2$R[11], cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)R[12], NR[13]R[14], C$_{3-8}$ cycloalkenyl or C$_{3-8}$ cycloalkyl;

R[9] is H, —S(O)$_2$R[11], —OC$_{1-6}$ alkyl, —SC$_{1-6}$ alkyl, —C$_{1-6}$ alkyl, —C$_{2-6}$ alkenyl, —C$_{2-6}$ alkynyl, C(O)R[12], C$_{3-8}$ cycloalkenyl or C$_{3-8}$ cycloalkyl;

R[10] is —C$_{1-6}$ alkyl, C$_{3-8}$ cycloalkyl, or C$_{3-8}$ cycloalkenyl;

R[11] is H, hydroxyl, —C$_{1-6}$ alkyl, C$_{3-8}$ cycloalkyl or C$_{3-8}$ cycloalkenyl;

R[12] is H, hydroxyl, —C$_{1-6}$ alkyl, C$_{3-8}$ cycloalkyl, C$_{3-8}$ cycloalkenyl, NR[13]R[14] or —OC$_{1-6}$ alkyl;

R[13] is H, —C$_{1-6}$ alkyl, C$_{3-8}$ cycloalkyl, C$_{3-8}$ cycloalkenyl SO$_2$R[11] or C(O)R[15];

R[14] is H, —C$_{1-6}$ alkyl, C$_{3-8}$ cycloalkenyl, aryl, heterocycle or C$_{3-8}$ cycloalkyl;

R[15] is H, —C$_{1-6}$ alkyl, C$_{3-8}$ cycloalkenyl or C$_{3-8}$ cycloalkyl; and R is H, —C$_{1-6}$ alkyl, C$_{3-8}$ cycloalkenyl or C$_{3-8}$ cycloalkyl;

with the provisos when " ---- " is a double bond then R[5] and R[6] are void; and the compound is not of structures

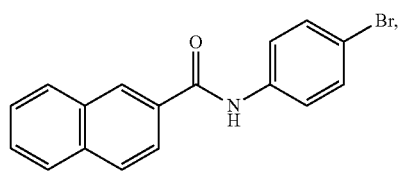

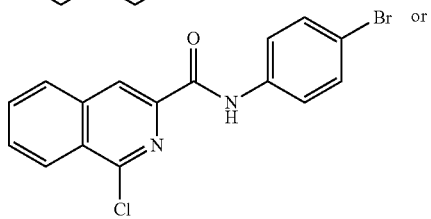

-continued

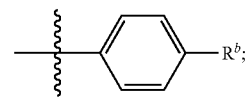

In another aspect, the invention provides a compound having Formula I wherein:

" $\overset{m}{\text{----}}$ " is a single bond or a double bond;

" $\overset{n}{\text{----}}$ " is a single bond or a double bond;

R[1] is H, halogen, nitro, cyano, —OC$_{1-6}$ alkyl, —SC$_{1-6}$ alkyl, —C$_{1-6}$ alkyl, C(O)R[12], NR[13]R[14], C$_{3-8}$ cycloalkyl, C$_{3-8}$ cycloalkenyl or hydroxyl;

R[2] is H, halogen, nitro, cyano, —OC$_{1-6}$ alkyl, —SC$_{1-6}$ alkyl, —C$_{1-6}$ alkyl, C(O)R[12], NR[13]R[14], C$_{3-8}$ cycloalkyl, C$_{3-8}$ cycloalkenyl or hydroxyl;

R[3] is H, halogen, nitro, cyano, —OC$_{1-6}$ alkyl, —SC$_{1-6}$ alkyl, —C$_{1-6}$ alkyl, C(O)R[12], NR[13]R[14], C$_{3-8}$ cycloalkyl, C$_{3-8}$ cycloalkenyl, C$_{6-10}$ aryl or hydroxyl;

R[4] is H or C(O)R[12];

R[5] is H, —OC$_{1-6}$ alkyl, —SC$_{1-6}$ alkyl or —C$_{1-6}$ alkyl;

R[6] is H, —OC$_{1-6}$ alkyl, —SC$_{1-6}$ alkyl or —C$_{1-6}$ alkyl;

Y is O;

X is NR;

R$^a$ is

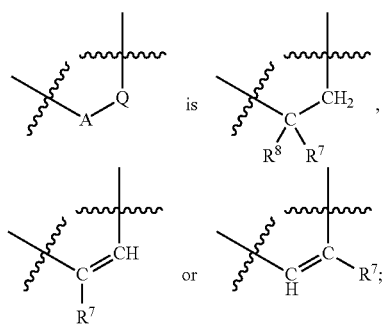

R$^b$ is bromine;

c is 0;

R[7] is H, halogen, nitro, cyano, —SC$_{1-6}$ alkyl, —C$_{1-6}$ alkyl, C(O)R[12], C$_{3-8}$ cycloalkenyl or C$_{3-8}$ cycloalkyl;

R[8] is H, halogen, cyano, —OC$_{1-6}$ alkyl, —SC$_{1-6}$ alkyl, —C$_{1-6}$ alkyl, C(O)R[12], NR[13]R[14], C$_{3-8}$ cycloalkenyl or C$_{3-8}$ cycloalkyl;

R[12] is H, hydroxyl, —C$_{1-6}$ alkyl, C$_{3-8}$ cycloalkyl, C$_{3-8}$ cycloalkenyl, NR[13]R[14] or —OC$_{1-6}$ alkyl;

R[13] is H, —C$_{1-6}$ alkyl, C$_{3-8}$ cycloalkyl, C$_{3-8}$ cycloalkenyl or C(O)R[15];

R[14] is H, —C$_{1-6}$ alkyl, C$_{3-8}$ cycloalkenyl, aryl, heterocycle or C$_{3-8}$ cycloalkyl;

R[15] is H, —C$_{1-6}$ alkyl, C$_{3-8}$ cycloalkenyl or C$_{3-8}$ cycloalkyl; and R is H;
with the provisos:
when " ------- " is a double bond then $R^5$ and $R^6$ are void; and
the compound is not of structures

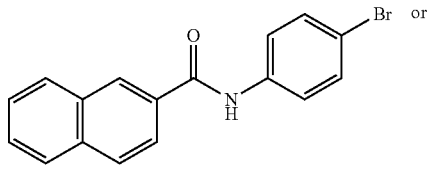

or

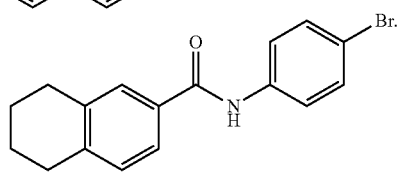

In another aspect, the invention provides a compound having Formula I wherein:
" $\overset{m}{-----}$ " is a double bond;
" $\overset{n}{-----}$ " is a double bond;
$R^1$ is H or —$C_{1-6}$ alkyl;
$R^2$ is H, halogen or —$C_{1-6}$ alkyl;
$R^3$ is H, $C_{6-10}$ aryl or —$C_{1-6}$ alkyl;
$R^4$ is $C(O)R^{12}$;
Y is O;
X is NR;
$R^a$ is

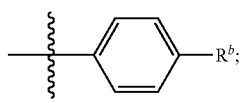

$R^b$ is bromine;
c is 0;

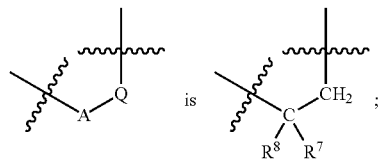

$R^7$ is H or $C_{1-6}$ alkyl;
$R^8$ is H or —$C_{1-6}$ alkyl;
$R^{12}$ is hydroxyl; and
R is H.
In another aspect, the invention provides a compound having Formula I wherein:
" $\overset{m}{-----}$ " is a double bond;
" $\overset{n}{-----}$ " is a double bond;
$R^1$ is H;
$R^2$ is H;
$R^3$ is H;
$R^4$ is H or $C(O)R^{12}$;
Y is O;
X is NR;
$R^a$ is

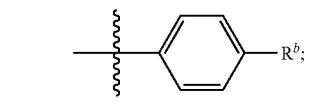

$R^b$ is bromine;
c is 0;

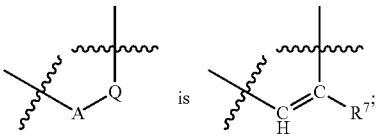

$R^7$ is H or $C(O)R^{12}$;
$R^{12}$ is hydroxyl;
R is H; and
the compound is not of structure

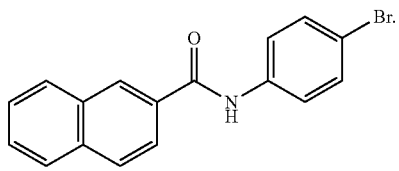 [SMILES: O=C(Nc1ccc(Br)cc1)c1ccc2ccccc2c1]

In another aspect, the invention provides a compound having Formula I wherein:
" $\overset{m}{-----}$ " is a double bond;
" $\overset{n}{-----}$ " is a double bond;
$R^1$ is H;
$R^2$ is H;
$R^3$ is H;
$R^4$ is $C(O)R^{12}$;
Y is O;
X is NR;
$R^a$ is

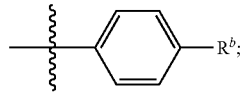

$R^b$ is bromine;
c is 0;

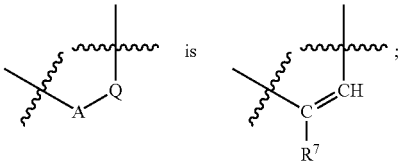

$R^7$ is $C_{1-6}$ alkyl;
$R^{12}$ is hydroxyl; and
R is H.

In another aspect, the invention provides a compound having Formula I
wherein:
"── m ──" is a single bond;
"── n ──" is a single bond;
$R^1$ is —$C_{1-6}$ alkyl;
$R^2$ is H;
$R^3$ is —$C_{1-6}$ alkyl;
$R^4$ is $C(O)R^{12}$;
$R^5$ is, —$C_{1-6}$ alkyl;
$R^6$ is, —$C_{1-6}$ alkyl;
Y is O;
X is NR;
$R^a$ is

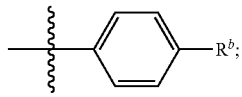

$R^b$ is bromine;
c is 0;

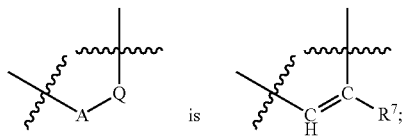

$R^7$ is $C(O)R^{12}$;
$R^{12}$ is hydroxyl; and
R is H.

The term "alkyl", as used herein, refers to saturated, monovalent or divalent hydrocarbon moieties having linear or branched moieties or combinations thereof and containing 1 to 6 carbon atoms. One methylene (—$CH_2$—) group, of the alkyl can be replaced by oxygen, sulfur, sulfoxide, nitrogen, carbonyl, carboxyl, sulfonyl, sulfate, sulfonate, —C(O)NH—, —S(O)$_2$NH—, by a divalent $C_{3-6}$ cycloalkyl, by a divalent heterocycle, or by a divalent aryl group. Alkyl groups can be independently substituted by halogen atoms, hydroxyl, cycloalkyl, amino, heterocyclic groups, carboxylic acid groups, phosphonic acid groups, sulphonic acid groups, phosphoric acid groups, nitro groups, amide groups, sulfonamides groups.

The term "cycloalkyl", as used herein, refers to a monovalent or divalent group of 3 to 8 carbon atoms derived from a saturated cyclic hydrocarbon. Cycloalkyl groups can be monocyclic or polycyclic. One methylene (—$CH_2$—) group, of the cycloalkyl can be replaced by a divalent $C_{3-6}$ cycloalkyl, by a divalent heterocycle, or by a divalent aryl group. Cycloalkyl can be independently substituted by halogen, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, ketone groups, aldehyde groups, amine groups, $C_{3-8}$ cycloalkyl groups or hydroxyl groups.

The term "cycloalkenyl", as used herein, refers to a monovalent or divalent group of 3 to 8 carbon atoms derived from a saturated cycloalkyl having at least one double bond. Cycloalkenyl groups can be monocyclic or polycyclic. One methylene (—$CH_2$—) group, of the cycloalkenyl can be replaced, by a divalent $C_{3-6}$ cycloalkyl, by a divalent heterocycle, or by a divalent aryl group. Cycloalkenyl groups can be independently substituted by halogen, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, ketone groups, aldehyde groups, amino groups, $C_{3-8}$ cycloalkyl groups or hydroxyl groups.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. One methylene (—$CH_2$—) group, of the alkenyl can be replaced by oxygen, sulfur, sulfoxide, nitrogen, carbonyl, carboxyl, sulfonyl, sulfate, sulfonate, amide, sulfonamide, by a divalent $C_{3-6}$ cycloalkyl, by a divalent heterocycle, or by a divalent aryl group. $C_{2-6}$ alkenyl can be in the E or Z configuration. Alkenyl groups can be substituted by $C_{1-3}$ alkyl, as defined above, or by halogen.

The term "alkynyl", as used herein, refers to a monovalent or divalent hydrocarbon radical having 2 to 6 carbon atoms, derived from a saturated alkyl, having at least one triple bond. One methylene (—$CH_2$—) group, of the alkynyl can be replaced by oxygen, sulfur, sulfoxide, nitrogen, carbonyl, carboxyl, sulfonyl, sulfate, sulfonate, amide, sulfonamide, by a divalent $C_{3-6}$ cycloalkyl, by a divalent heterocycle, or by a divalent aryl group. Alkynyl groups can be substituted by $C_{1-3}$ alkyl, as defined above, or by halogen.

The term "heterocycle" as used herein, refers to a 3 to 10 membered ring, which can be aromatic or non-aromatic, saturated or unsaturated, containing at least one heteroatom selected form oxygen, nitrogen, sulfur, sulfoxide, carbonyl, carboxyl, sulfonyl, sulfate, sulfonate, amide, sulfonamide, or combinations of at least two thereof, interrupting the carbocyclic ring structure. One methylene (—$CH_2$—) group of the heterocycle can be interrupted by a divalent $C_{3-6}$ cycloalkyl, by a divalent heterocycle, or by a divalent aryl group. The heterocyclic ring can be saturated or unsaturated. The heterocyclic ring can be interrupted by a C═O; the S and N heteroatoms can be oxidized. Heterocycles can be monocyclic or polycyclic. Heterocyclic ring moieties can be substituted by halogen, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, ketone groups, aldehyde groups, amine groups, $C_{3-8}$ cycloalkyl groups, $C_{3-8}$ cycloalkenyl groups or hydroxyl groups.

The term "aryl" as used herein, refers to an organic moiety derived from an aromatic hydrocarbon consisting of a ring containing 6 to 10 carbon atoms by removal of one hydrogen, which can be substituted by halogen, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, ketone groups, aldehyde groups, amine groups, $C_{3-8}$ cycloalkyl groups or hydroxyl groups. Usually aryl is phenyl. Preferred substitution site on aryl are the meta and the para positions. Most preferred substitution sites on aryl are the para positions.

The term "hydroxyl" as used herein, represents a group of formula "—OH".

The term "carbonyl" as used herein, represents a group of formula "—C(O)—".

The term "carboxyl" as used herein, represents a group of formula "—C(O)O—".

The term "sulfonyl" as used herein, represents a group of formula "—$SO_2$—".

The term "sulfate" as used herein, represents a group of formula "—O—S(O)$_2$—O—".

The term "sulfonate" as used herein, represents a group of the formula "—S(O)$_2$—O—".

The term "ester" as used herein, represents a group of formula "—C(O)OR$^x$", wherein R$^x$ can be alkyl, aryl, cycloalkyl, cycloalkenyl, heterocyle as defined above.

The term "ketone" as used herein, represents a group of formula "—C(O)R$^x$", wherein R$^x$ can be alkyl, aryl, cycloalkyl, cycloalkenyl heterocycle as defined above.

The term "amine" as used herein, represents a group of formula "—NR$^x$R$^y$", wherein R$^x$ and R$^y$ can be independently can be H, alkyl, aryl, cycloalkyl, cycloalkenyl heterocycle as defined above.

The term "aldehyde" as used herein, represents a group of formula "—C(O)H",

The term "carboxylic acid" as used herein, represents a group of formula "—C(O)ON".

The term "nitro" as used herein, represents a group of formula "—NO$_2$".

The term "cyano" as used herein, represents a group of formula "—CN".

The term "amide" as used herein, represents a group of formula "—C(O)NR$^x$R$^y$," wherein R$^x$ and R$^y$ can be independently H, alkyl, aryl, cycloalkyl, cycloalkenyl heterocycle as defined above.

The term "sulfonamide" as used herein, represents a group of formula "—S(O)$_2$NR$^x$R$^y$" wherein R$^x$ and R$^y$ can be independently H, alkyl, aryl, cycloalkyl, cycloalkenyl, heterocycle as defined above.

The term "sulfoxide" as used herein, represents a group of formula "—S(O)—".

The term "phosphonic acid" as used herein, represents a group of formula "—P(O)(OH)$_2$".

The term "phosphoric acid" as used herein, represents a group of formula "—OP(O)(OH)$_2$".

The term "sulphonic acid" as used herein, represents a group of formula "—S(O)2OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Compounds of the invention are:
2-{[(4-Bromophenyl)amino]carbonyl}-7-tert-butyl-3,4-dihydronaphthalene-1-carboxylic acid;
2-{[(4-Bromophenyl)amino]carbonyl}-5-isopropyl-3,4-dihydronaphthalene-1-carboxylic acid;
2-{[(4-Bromophenyl)amino]carbonyl}-4,4-dimethyl-3,4-dihydronaphthalene-1-carboxylic acid;
2-{[(4-Bromophenyl)amino]carbonyl}-6-chloro-3,4-dihydronaphthalene-1-carboxylic acid;
2-{[(4-Bromophenyl)amino]carbonyl}-3,4-dihydronaphthalene-1-carboxylic acid;
2-{[(4-Bromophenyl)amino]carbonyl}-5,8-dimethyl-3,4-dihydronaphthalene-1-carboxylic acid;
2-{[(4-Bromophenyl)amino]carbonyl}-5,7-dimethyl-3,4-dihydronaphthalene-1-carboxylic acid;
2-{[(4-Bromophenyl)amino]carbonyl}-5-phenyl-3,4-dihydronaphthalene-1-carboxylic acid
2-{[(4-Bromophenyl)amino]carbonyl}-1-naphthoic acid;
2-{[(4-Bromophenyl)amino]carbonyl}-4-ethyl-1-naphthoic acid.
3-{[(4-Bromophenyl)amino]carbonyl}-5,5,8,8-tetramethyl-5,6,7,8-tetrahydronaphthalene-2-carboxylic acid;
3-{[(4-Bromophenyl)amino]carbonyl}-2-naphthoic acid.

Preferred compounds of the invention are:
2-{[(4-Bromophenyl)amino]carbonyl}-7-tert-butyl-3,4-dihydronaphthalene-1-carboxylic acid;
2-{[(4-Bromophenyl)amino]carbonyl}-5-isopropyl-3,4-dihydronaphthalene-1-carboxylic acid;
2-{[(4-Bromophenyl)amino]carbonyl}-4,4-dimethyl-3,4-dihydronaphthalene-1-carboxylic acid;
2-{[(4-Bromophenyl)amino]carbonyl}-7-chloro-3,4-dihydronaphthalene-1-carboxylic acid;
2-{[(4-Bromophenyl)amino]carbonyl}-3,4-dihydronaphthalene-1-carboxylic acid;
2-{[(4-Bromophenyl)amino]carbonyl}-5,8-dimethyl-3,4-dihydronaphthalene-1-carboxylic acid;
2-{[(4-Bromophenyl)amino]carbonyl}-5,7-dimethyl-3,4-dihydronaphthalene-1-carboxylic acid;
2-{[(4-Bromophenyl)amino]carbonyl}-5-phenyl-3,4-dihydronaphthalene-1-carboxylic acid;
2-{[(4-Bromophenyl)amino]carbonyl}-4-ethyl-1-naphthoic acid.

Most Preferred compounds of the invention are:
2-{[(4-Bromophenyl)amino]carbonyl}-4,4-dimethyl-3,4-dihydronaphthalene-1-carboxylic acid;
2-{[(4-bromophenyl)amino]carbonyl}-5,8-dimethyl-3,4-dihydronaphthalene-1-carboxylic acid;
2-{[(4-Bromophenyl)amino]carbonyl}-4-ethyl-1-naphthoic acid.

Some compounds of Formula I and some of their intermediates have at least one asymmetric center in their structure. This asymmetric center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic and the like (Handbook of Pharmaceutical Salts, P. Heinrich Stahal& Camille G. Wermuth (Eds), Verlag Helvetica Chemica Acta-Zürich, 2002, 329-345).

The base addition salt form of a compound of Formula I that occurs in its acid form can be obtained by treating the acid with an appropriate base such as an inorganic base, for example, sodium hydroxide, magnesium hydroxide, potassium hydroxide, Calcium hydroxide, ammonia and the like; or an organic base such as for example, L-Arginine, ethanolamine, betaine, benzathine, morpholine and the like. (Handbook of Pharmaceutical Salts, P. Heinrich Stahal& Camille G. Wermuth (Eds), Verlag Helvetica Chemica Acta-Zürich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the N-formyl peptide receptor like-1 receptor.

In another embodiment, there are provided pharmaceutical compositions including at least one compound of the invention in a pharmaceutically acceptable carrier.

In a further embodiment of the invention, there are provided methods for treating disorders associated with modulation of the N-formyl peptide receptor like-1 receptor.

Such methods can be performed, for example, by administering to a subject in need thereof a pharmaceutical composition containing a therapeutically effective amount of at least one compound of the invention.

Therapeutic utilities of the N-formyl peptide receptor like-1 receptor modulators are ocular inflammatory diseases including, but not limited to, wet and dry age-related macular degeneration (ARMD), uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema; infectious keratitis, uveitis, corneal wound healing, ocular inflammation, herpetic keratitis, corneal angiogenesis, lymphangiogenesis, uveitis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vasuclar diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, post surgical corneal wound healing, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with accosiated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, eczema, psoriasis, CNS disorders such as Alzheimer's disease, arthritis, sepsis, inflammatory bowel disease, cachexia, angina pectoris, post-surgical corneal inflammation, blepharitis, MGD, dermal wound healing, burns, rosacea, atopic dermatitis, acne, psoriasis, seborrheic dermatitis, actinic keratoses, viral warts, photoaging rheumatoid arthritis and related inflammatory disorders, alopecia, glaucoma, branch vein occlusion, Best's vitelliform macular degenartion, retinitis pigmentosa, proliferative vitreoretinopathy (PVR), and any other degenerative disease of either the photoreceptors or the RPE (Perretti, Mauro et al. Pharmacology & Therapeutics 127 (2010) 175-188.)

These compounds are useful for the treatment of mammals, including humans, with a range of conditions and diseases that are alleviated by the N-formyl peptide receptor like-1 receptor modulation: including, but not limited to the treatment of wet and dry age-related macular degeneration (ARMD), diabetic retinopathy (proliferative), retinopathy of prematurity (ROP), diabetic macular edema, uveitis, retinal vein occlusion, cystoids macular edema, glaucoma, branch vein occlusion, Best's vitelliform macular degenartion, retinitis pigmentosa, proliferative vitreoretinopathy (PVR), and any other degenerative disease of either the photoreceptors or the RPE.

In still another embodiment of the invention, there are provided methods for treating disorders associated with modulation of the FPRL-1 receptor. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or a pharmaceutically acceptable salt thereof, for the manufacture of a medicament for the treatment of ocular inflammatory diseases including, but not limited to, wet and dry age-related macular degeneration (ARMD), uveitis, corneal wound healing, ocular inflammation, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema; infectious keratitis, uveitis, herpetic keratitis, corneal angiogenesis, lymphangiogenesis, uveitis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vasuclar diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, post surgical corneal wound healing, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with accosiated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigement epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, eczema, psoriasis, CNS disorders such as Alzheimer's disease, arthritis, sepsis, inflammatory bowel disease, cachexia, angina pectoris, post-surgical corneal inflammation, blepharitis, MGD, dermal wound healing, burns, rosacea, atopic dermatitis, acne, psoriasis, seborrheic dermatitis, actinic keratoses, viral warts, photoaging rheumatoid arthritis and related inflammatory disorders, alopecia, glaucoma, branch vein occlusion, Best's vitelliform macular degenartion, retinitis pigmentosa, proliferative vitreoretinopathy (PVR), and any other degenerative disease of either the photoreceptors or the RPE.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, direct injection, application at the back of the eye or formulations that may further enhance the long duration of actions such as a slow releasing pellet, suspension, gel, or sustained delivery devices such as any suitable drug delivery system (DDS) known in the art. While topical administration is preferred, this compound may also be used in an intraocular implant as described in U.S. Pat. No. 7,931,909, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual nontoxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

The compounds of the invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of the N-formyl peptide receptor like-1 (FPRL-1) receptor.

Thus, in further embodiments of the invention, there are provided methods for treating a disorder associated with modulation of the N-formyl peptide receptor like-1 (FPRL-1) receptor. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of formula I according to the invention can be prepared analogously to conventional methods as understood by the person skilled in the art of synthetic organic chemistry. Synthetic Scheme 1 set forth below, illustrates how the compounds according to the invention can be made.

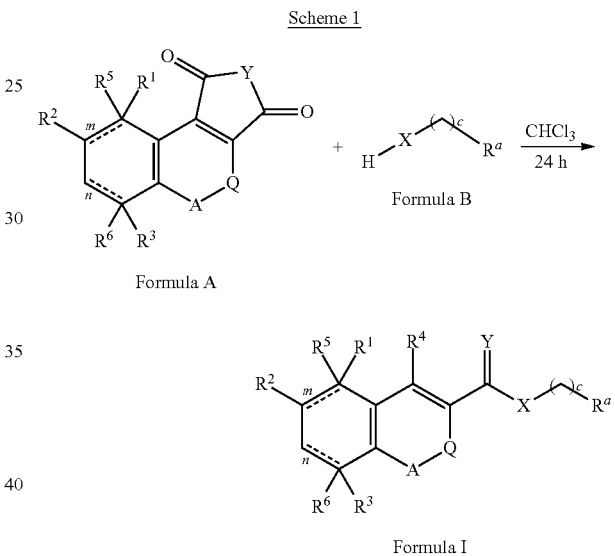

Scheme 1

Formula A

Formula B

Formula I

Compounds within the scope of the invention may be prepared as depicted in Scheme 1. In general, a cyclic anhydride of the Formula A, can be reacted with an amino compound of Formula B, under conditions in which the amino group of Formula B reacts with the less hindered carbonyl of the anhydride moiety to provide compounds of Formula I. At this stage, those skilled in the art will appreciate that many additional compounds that fall under the scope of the invention may be prepared by performing various common chemical reactions. Details of certain specific chemical transformations are provided in the examples.

Those skilled in the art will be able to routinely modify and/or adapt the following scheme to synthesize any compounds of the invention covered by Formula I.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of hydrogen $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diastereoisomeric isomers, chromatographic separation may be employed.

Compound names were generated with ACD version 11.0; and Intermediates and reagent names used in the examples were generated with softwares such as Chem Bio Draw Ultra version 12.0, ACD version 11.0 or Auto Nom 2000 from MDL ISIS Draw 2.5 SP1.

In general, characterization of the compounds is performed according to the following methods:

NMR spectra are recorded on 300 or 600 MHz Varian and acquired at room temperature. Chemical shifts are given in ppm referenced either to internal TMS or to the solvent signal. The optical rotation was recorded on Perkin Elmer Polarimeter 341, 589 nm at 20° C., Na/Hal lamp.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

Usually the compounds of the invention were purified by column chromatography (Auto-column) on an Teledyne-ISCO CombiFlash with a silica column, unless noted otherwise.

The chiral resolution was performed using chiral HPLC:
Preparative methods: Chiralpak AD-H (2×15 cm)
  30% ethanol/CO2, 100 Bar
  65 ml/min, 220 nm.
Analytical method: Chiralpak AD-H (25×0.46 cm)
  40% ethanol (DEA)/CO$_2$, 100 Bar
  3 ml/min, 220 nm.
The following abbreviations are used in the examples:

$CH_2Cl_2$ dichloromethane
EtOAc ethyl acetate
PPA phenolpropanolamine
$NaHCO_3$ sodium bicarbonate
$K_2CO_3$ potassium carbonate
$CDCl_3$ deuterated chloroform
Pd/C palladium(0) on carbon
THF tetrahydrofuran
AcOH acetic acid
$Pd(OAc)_2$ palladium acetate
NaOH sodium hydroxide
MeOH methanol
HCl hydrochloric acid
$CD_3OD$ deuterated methanol
$CD_3COCD_3$ deuterated acetone
$Ac_2O$ acetic anhydride
DCC N,N'-Dicyclohexylcarbodiimide
RT room temperature
$CHCl_3$ chloroform The following synthetic schemes illustrate how compounds according to the invention can be made. Those skilled in the art will be routinely able to modify and/or adapt the following schemes to synthesize any compound of the invention covered by Formula I.

Example 1

Intermediate 1

Dimethyl 5-bromo-3,4-dihydronaphthalene-1,2-dicarboxylate

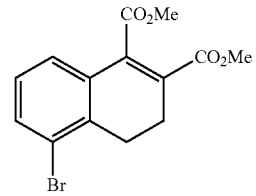 [SMILES: COC(=O)C1=C(C(=O)OC)c2cccc(Br)c2CC1]

A solution of 2-bromo-styrene (2.2 g, 12.9 mmol), dimethyl acetylenedicarboxylate (520 mg, 3.7 mmol) and N,N-dimethylformamide-dimethylacetal (60 mg) was placed in a high-pressure glass tube and the vessel was sealed with a Teflon screw cap. The solution was heated to 110° C. for 5 h. This crude syrup was diluted with $CH_2Cl_2$ (1 mL) and purified by silica gel chromatography using 100% hexane, followed by 7.5% EtOAc in hexane. Intermediate 1 was isolated as a thick oil.

$^1$HNMR ($CDCl_3$): δ 2.67 (t, J=7.8 Hz, 2H), 3.00 (t, J=7.8 Hz, 2H), 3.82 (s, 3H), 3.93 (s, 3H), 7.09 (t, J=7.5 Hz, 1H), 7.13 (dd, J=1.8, 7.5 Hz, 1H), 7.53 (dd, J=1.8, 7.5 Hz, 1H).

Intermediates 2 and 3 were prepared from the corresponding starting materials and in a similar manner to the procedure described in Example 1 for Intermediate 1. The reagents, reactants used and the results are described below in Table 1.

TABLE 1

| Intermediate number | IUPAC name Structure | Reagent(s) Reactant(s) | $^1$H NMR δ (ppm) for Intermediate |
|---|---|---|---|
| 2 | Dimethyl 7-chloro-3,4-dihydronaphthalene-1,2-dicarboxylate | 4-chloro-styrene | $^1$HNMR (CDCl$_3$): δ 2.61 (t, J = 7.4 Hz, 2H), 2.83 (t, J = 7.4 Hz, 2H), 3.81 (s, 3H), 3.95 (s, 3H), 7.12 (d, J = 7.8 Hz, 1H), 7.15 (d, J = 1.5 Hz, 1H), 7.26 (dd, J = 7.8, 1.5 Hz, 1H). |
| 3 | Dimethyl 5,7-dimethyl-3,4-dihydronaphthalene-1,2-dicarboxylate | 1-ethenyl-2,4-dimethyl-benzene [CAS 2234-20-0] | $^1$HNMR (CDCl$_3$): δ 2.26 (s, 3H), 2.27 (s, 3H), 2.64 (t, J = 7.8 Hz, 2H), 2.76 (t, J = 7.8 Hz, 2H), 3.80 (s, 3H), 3.94 (s, 3H), 6.82 (s, 1H), 6.99 (s, 1H). |

Example 2

Intermediate 4

Diethyl 4-ethylnaphthalen-1,2-dicarboxylate

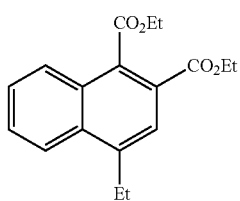 [SMILES: CCOC(=O)c1cc(CC)c2ccccc2c1C(=O)OCC]

A mixture of diethyl 2-oxo-3-((1-phenylcyclopropyl)methyl)succinate [CAS 50462-74-3] (1.27 g, 4 mmol) and PPA (25 g) was stirred with a glass rod every 5 min for 1 h. The reaction was quenched with ice, and the products were extracted with ether. The ether extract was washed with aq. NaHCO$_3$, and dried, and the solvent was removed under reduced pressure. The crude material was purified by silica gel chromatography. Intermediate 4 was isolated as a yellow solid.

$^1$H NMR (CDCl$_3$): δ 1.34 (t, J=9.0 Hz, 3H), 1.40 (t, J=6.0 Hz, 3H), 1.42 (t, J=9.0 Hz, 3H), 3.07 (q, J=6.0 Hz, 2H), 4.41 (q, J=9.0 Hz, 2H), 4.55 (t, J=9.0 Hz, 1H), 7.51-7.60 (m 2H), 7.85 (s, 1H), 7.95 (d, J=9.0 Hz, 1H), 8.03 (d, J=9.0 Hz, 1H).

Example 3

Intermediate 5

Dimethyl 5-(prop-1-en-2-yl)-3,4-dihydronaphthalene-1,2-dicarboxylate

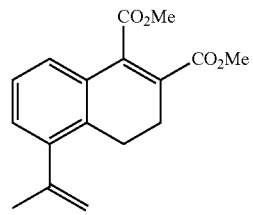 [SMILES: C=C(C)c1cccc2c1CCC(C(=O)OC)=C2C(=O)OC]

Intermediate 1 (215 mg, 0.66 mmol), 4,4,5,5-tetramethyl-2-(prop-1-en-2-yl)-1,3,2-dioxaborolane [CAS 126726-62-3] (916 mg), Pd(PPh$_3$)$_4$ (60 mg), 2M K$_2$CO$_3$ in water (1 mL) and dimethoxyethane (10 mL) were heated to 90° C. for 5 h. The reaction mixture was diluted with water (15 mL), and the products were extracted with EtOAc (3×30 mL). The combined organic layers were washed with brine (10 mL), and dried, and the solvent was evaporated. The product was purified by silica gel chromatography using 7.5% EtOAc in hexane. Intermediate 5 was isolated as a white solid.

$^1$HNMR (CDCl$_3$): δ 2.02 (s, 3H), 2.57 (t, J=7.5 Hz, 2H), 2.85 (t, J=7.5 Hz, 2H), 3.81 (s, 3H), 3.94 (s, 3H), 4.84 (s, 1H), 5.84 (s, 1H), 7.09 (dd, J=2.1, 7.2 Hz, 1H), 7.15 (dd, J=2.1, 7.2 Hz, 1H), 7.19 (t, J=7.2 Hz, 1H).

Intermediate 6 was prepared from the corresponding starting materials and in a similar manner to the procedure described in Example 3 for Intermediate 5. The reagents, reactants used and the results are described below in Table 2.

TABLE 2

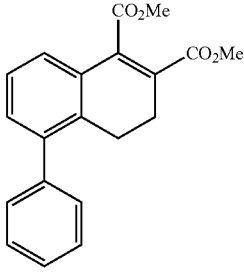

| Intermediate number | IUPAC name Structure | Reagent Reactant | $^1$H NMR δ (ppm) for Intermediate | Characteristic |
|---|---|---|---|---|
| 6 | Dimethyl 5-phenyl-3,4-dihydronaphthalene-1,2-dicarboxylate | phenyl boronic acid Pd(PPh$_3$)$_4$ | $^1$HNMR (CDCl$_3$): δ 2.52 (t, J = 7.8 Hz, 2H), 2.78 (t, J = 7.8 Hz, 2H), 3.80 (s, 3H), 3.96 (s, 3H), 7.20 (t, J = 4.8 Hz, 1H), 7.26-7.29 (m, 4H), 7.36 (t, J = 7.8 Hz, 1H), 7.42 (t, J = 7.8 Hz, 2H). | MS (C$_{20}$H$_{18}$O$_4$; MWt. 322): Observed M + 23 = 345 |

Example 4

Intermediate 7

Dimethyl 5-(isopropyl)-3,4-dihydronaphthalene-1,2-dicarboxylate

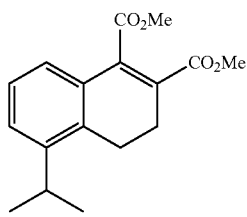 [SMILES: COC(=O)C1=C(C(=O)OC)c2cccc(C(C)C)c2CC1]

To a solution of Intermediate 5 (150 mg, 0.52 mmol) in EtOAc (5 mL) was added 10% Pd-C (10 mg) and the mixture was stirred under a hydrogen atmosphere in a PARR hydrogenator at 60 psi for 24 hours. The Pd-C was filtered off, and the solvent removed by distillation. Intermediate 7 was isolated as a white solid.

$^1$HNMR (CDCl$_3$): δ 1.23 (d, J=6.9 Hz, 6H), 2.63 (t, J=7.5 Hz, 2H), 2.88 (t, J=7.5 Hz, 2H), 3.20 (septet, J=6.9 Hz, 1H), 3.81 (s, 3H), 3.94 (s, 3H), 7.03 (d, J=7.5 Hz, 1H), 7.21 (t, J=7.5 Hz, 1H), 7.30 (d, J=7.5 Hz, 1H).

Example 5

Intermediate 8

Ethyl 4,4-dimethyl-1-oxo-1,2,3,4-tetrahydronaphthalene-2-carboxylate

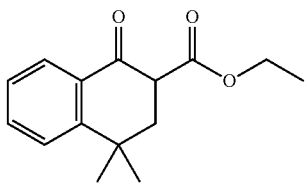 [SMILES: CCOC(=O)C1CC(C)(C)c2ccccc2C1=O]

To a suspension of NaH (290 mg, 12.08 mmol) in THF (15 mL) was added diethyl carbonate (1.4 mL, 11.5 mmol). A solution of 3,4-dihydro-4,4-dimethyl-1(2H)-naphthalenone [CAS 2979-69-3] (1.0 g, 5.75 mmol) in THF (5 mL) was added, and the mixture was refluxed for 18 h. The mixture was cooled to ambient temperature. The reaction was diluted with ether, water was added carefully, followed by 3 mL of AcOH. The product was extracted with ether, and washed with brine, and dried, and the solvent removed under reduced pressure. The crude mixture was purified by silica gel chromatography (10% EtOAc in hexane). Intermediate 8 was isolated as a yellow oil.

$^1$H NMR (CDCl$_3$): δ 1.30 (s, 6H), 1.36 (t, J=7.2 Hz, 3H), 2.50 (s, 2H), 4.30 (q, J=7.2 Hz, 2H), 7.20-7.38 (m, 3H), 7.87 (d, J=7.6 Hz, 1H).

Example 6

Intermediate 9

Ethyl 4,4-dimethyl-1-{[(trifluoromethyl)sulfonyl]oxy}-3,4-dihydronaphthalene-2-carboxylate

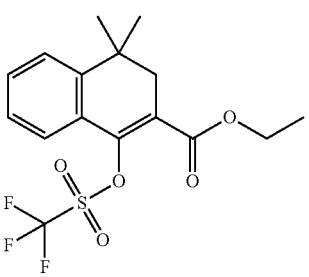 [SMILES: CCOC(=O)C1=C(OS(=O)(=O)C(F)(F)F)c2ccccc2C(C)(C)C1]

To a solution of Intermediate 8 (678 mg, 2.76 mmol) in ether was added NaH (130 mg, 5.52 mmol) in small portions and the reaction was stirred for 5 min. Then triflic anhydride (0.55 mL, 3.31 mmol) was added drop wise and stirred for 30 min. The reaction was quenched by adding water carefully to the reaction, extracted with ether, washed with brine, dried and solvent removed. Intermediate 9 was isolated after silicagel column purification, 10% EtOAc in hexane.

$^1$H NMR (CDCl$_3$) δ ppm 1.24 (s, 6H), 1.36 (t, J=6.0 Hz, 3H), 2.65 (s, 2H), 4.31 (q, J=6.0 Hz, 2H), 7.18-7.40 (m, 3H), 7.48 (d, J=6.0 Hz, 1H).

Example 7

Intermediate 10

2-Ethyl 1-methyl 4,4-dimethyl-3,4-dihydronaphthalene-1,2-dicarboxylate

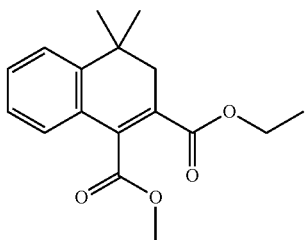 [SMILES: CCOC(=O)C1=C(C(=O)OC)c2ccccc2C(C)(C)C1]

A mixture of Intermediate 9 (916 mg, 2.4 mmol), 1,3-bis(diphenylphosphino)propane (15 mg, 0.03 mmol), Pd(OAc)$_2$ (20 mg), Et$_3$N (1.5 mL), MeOH (2.0 mL) and DMF (5.0 mL) was stirred at 90° C. under a carbon monoxide atmosphere for 48 h. The solvent was removed, and the product was purified by silica gel chromatography (10% EtOAc in hexane). Intermediate 10 was isolated as a yellow oil.

$^1$H NMR (CDCl$_3$) δ 1.29 (s, 6H), 1.32 (t, J=6.6 Hz, 3H), 2.56 (s, 2H), 3.92 (s, 3H), 4.25 (q, J=6.6 Hz, 2H), 7.13-7.25 (m, 2H), 7.30-7.40 (m, 2H).

Example 8

Intermediate 11

5-(isopropyl)-3,4-dihydronaphthalene-1,2-dicarboxylic Acid

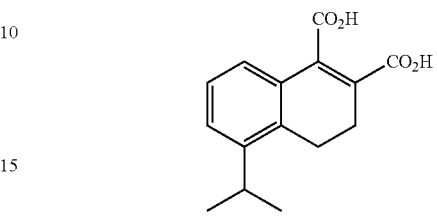

To a solution of Intermediate 7 (140 mg, 0.48 mmol) in MeOH (2 mL) was added a solution of NaOH (320 mg, 8 mmol) in water (2 mL). The mixture was heated to 100° C. for 8 h. The crude reaction mixture was diluted with CH$_2$Cl$_2$ (5 mL) and 10% aqueous HCl was added until the solution was acidic. The product was extracted with CH$_2$Cl$_2$ (25 mL), and the organic layer separated. The solvent was evaporated. Intermediate 11 was isolated as a pale yellow solid.

$^1$HNMR (CD$_3$OD): δ 1.24 (d, J=6.6 Hz, 6H), 2.59 (t, J=7.5 Hz, 2H), 2.89 (t, J=7.5 Hz, 2H), 3.26 (septet, J=6.6 Hz, 1H), 7.12 (d, J=7.2 Hz, 1H), 7.22 (t, J=7.2 Hz, 1H), 7.34 (d, J=7.2 Hz, 1H).

Intermediates 12, 13, 14, 15 and 16 were prepared from the corresponding starting materials and in a similar manner to the procedure described in Example 8 for Intermediate 11. The reagents, reactants used and the results are described below in Table 3.

TABLE 3

| Intermediate number | IUPAC name Structure | Reactant | $^1$H NMR δ (ppm) for Intermediate |
|---|---|---|---|
| 12 | 7-Chloro-3,4-dihydronaphthalene-1,2-dicarboxylic acid | Intermediate 2 | |
| 13 | 5-Phenyl-3,4-dihydronaphthalene-1,2-dicarboxylic acid | Intermediate 6 | $^1$HNMR (CD$_3$OD): δ 2.50 (t, J = 8.4 Hz, 2H), 2.77 (t, J = 8.4 Hz, 2H), 7.25-7.33 (m, 5H), 7.36-7.44 (m, 3H) |

TABLE 3-continued

| Intermediate number | IUPAC name Structure | Reactant | $^1$H NMR δ (ppm) for Intermediate |
|---|---|---|---|
| 14 | 4-Ethylnaphthalen-1,2-dicarboxylic acid | Intermediate 4 | $^1$H NMR (CD$_3$OD): δ 1.37 (t, J = 6.0 Hz, 3H), 3.14 (q, J = 6.0 Hz, 2H), 7.51-7.69 (m, 2H), 7.90 (s, 1H), 8.01 (d, J = 6.0 Hz, 1H), 8.14 (d, J = 6.0 Hz, 1H). |
| 15 | 4,4-Dimethyl-3,4-dihydronaphthalene-1,2-dicarboxylic acid | Intermediate 10 | |
| 16 | 5,7-Dimethyl-3,4-dihydronaphthalene-1,2-dicarboxylic acid | Intermediate 3 | $^1$HNMR (CD$_3$COCD$_3$): δ 2.25 (s, 3H), 2.26 (s, 3H), 2.62 (t, J = 9.0 Hz, 2H), 2.73 (t, J = 9.0 Hz, 2H), 7.01 (s, 1H), 7.03 (s, 1H). |

Example 9

Intermediate 17

6-Isopropyl-4,5-dihydronaphtho[1,2-c]furan-1,3-dione

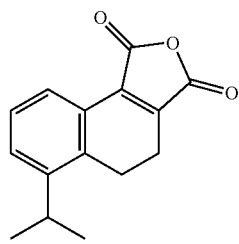 [SMILES: CC(C)c1cccc2c1CCC1=C2C(=O)OC1=O]

To Intermediate 11 (120 mg, 0.48 mmol, cooled to −78° C.) was added Ac$_2$O (4 mL). The cooling bath was removed, and the solution was stirred at ambient temperature for 4 h. The crude solution turned turbid. At this point, the crude mixture was passed through a short silica gel (1 g) column. The solvent was removed on a rotary evarorator. Intermediate 17 was used as is in the next step.

Intermediates 18, 19 and 20 were prepared from the corresponding starting materials and in a similar manner to the procedure described in Example 9 for Intermediate 17 and used in the next step. The reactants used are described below in Table 4.

TABLE 4

| Intermediate number | IUPAC name Structure | Reactant |
|---|---|---|
| 18 | 8-Chloro-4,5-dihydronaphtho[1,2-c]furan-1,3-dione | Intermediate 12 |
| 19 | 6-Phenyl-4,5-dihydronaphtho[1,2-c]furan-1,3-dione | Intermediate 13 |

TABLE 4-continued

| Intermediate number | IUPAC name Structure | Reactant |
|---|---|---|
| 20 | 6,8-Dimethyl-4,5-dihydronaphtho[1,2-c]furan-1,3-dione 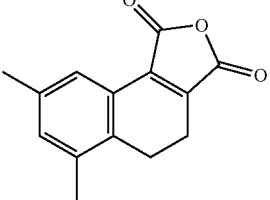 | Intermediate 16 |

TABLE 5

| Intermediate number | IUPAC name Structure | Reagent Reactant | $^1$H NMR δ (ppm) for Intermediate |
|---|---|---|---|
| 22 | 4-Ethylnaphtho(1,2-c)furan-1,3-dione 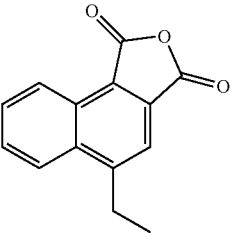 | Intermediate 14 | $^1$H NMR (CDCl$_3$): δ 1.46 (t, J = 9.0 Hz, 3H), 3.26 (q, J = 9.0 Hz, 2H), 7.75-7.85 (m, 3H), 8.15-8.27 (m, 1H), 8.75-8.90 (m, 1H). |

Example 10

Intermediate 21

5,5-Dimethyl-4,5-dihydronaphtho[1,2-c]furan-1,3-dione

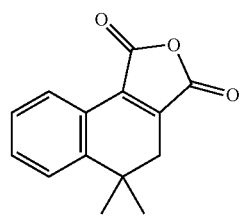 [SMILES: CC1(C)CC2=C(C(=O)OC2=O)c2ccccc21]

A solution of Intermediate 15 (220 mg, 0.9 mmol), DCC (190 mg, 0.9 mmol) and acetone (5 mL) was stirred at RT for 18 h. The solvent was removed, and the crude Intermediate 21 was used as is in the next step.

Intermediate 22 was prepared from the corresponding starting materials and in a similar manner to the procedure described in Example 10 for Intermediate 21. The reagents, reactants used and the results are described below in Table 5.

Example 11

Compound 1

2-{[(4-Bromophenyl)amino]carbonyl}-5-isopropyl-3,4-dihydronaphthalene-1-carboxylic Acid

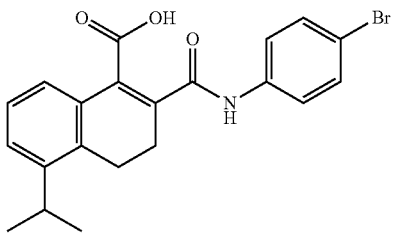 [SMILES: CC(C)c1cccc2c1CCC(C(=O)Nc1ccc(Br)cc1)=C2C(=O)O]

To a solution of Intermediate 17 (105 mg, 0.44 mmol) in CHCl$_3$ (3 mL) was added 4-bromo aniline (82 mg, 0.5 mmol) in CHCl$_3$ (1 mL). The mixture was stirred for 24 h. A solid separated, this solid was filtered and dried. Desired Compound 1 was obtained.

$^1$HNMR (CD$_3$OD): δ 1.24 (d, J=6.6 Hz, 6H), 2.64 (t, J=7.2 Hz, 2H), 2.94 (t, J=7.2 Hz, 2H), 3.26 (septet, J=6.6 Hz, 1H), 7.18 (d, J=6.9 Hz, 1H), 7.21 (t, J=6.9 Hz, 1H), 7.33 (d, J=6.9 Hz, 1H), 7.46 (d, J=8.7 Hz, 2H), 7.59 (d, J=8.7 Hz, 2H).

MS (C$_{21}$H$_{20}$BrNO$_3$; MWt. 413): Observed M−1=412 and 414

Compounds 2, 3, 4, 5, 6, 7, 8, 9, 10, 11 and 12 were prepared from the corresponding starting materials and in a similar manner to the procedure described in Example 11 for Compound 1. The reagents, reactants used and the results are described below in Table 6.

TABLE 6

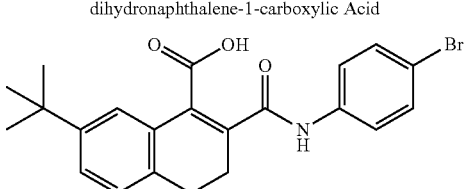

| Comp No. | IUPAC name Structure | Reagent(s) Reactant(s) | $^1$H NMR δ (ppm) for Compound | Characteristics |
|---|---|---|---|---|
| 2 | 2-{[(4-Bromophenyl)amino]carbonyl}-7-tert-butyl-3,4-dihydronaphthalene-1-carboxylic Acid | 8-(Tert-butyl)-4,5-dihydronaphtho[1,2-c]furan-1,3-dione [CAS 134030-26-5] | $^1$HNMR (CD$_3$SOCD$_3$): δ 1.24 (s, 9H), 2.56 (t, J = 8.1 Hz, 2H), 2.78 (t, J = 8.1 Hz, 2H), 7.18 (d, J = 8.1 Hz, 1H), 7.29 (s, 1H), 7.31 (d, J = 8.1 Hz, 1H), 7.49 (d, J = 8.7 Hz, 2H), 7.61 (d, J = 8.7 Hz, 2H). | MS (C$_{22}$H$_{22}$BrNO$_3$; MWt. 427): Observed M − 1 = 426 and 428 |

TABLE 6-continued

| Comp No. | IUPAC name Structure | Reagent(s) Reactant(s) | ¹H NMR δ (ppm) for Compound | Characteristics |
|---|---|---|---|---|
| 3 | 2-{[(4-Bromophenyl)amino]carbonyl}--4,4-dimethyl-3,4-dihydronaphthalene-1-carboxylic Acid | Intermediate 21 | ¹HNMR (CD₃OD): δ 1.33 (s, 6H), 2.55 (s, 2H), 7.10-7.40 (m, 4H), 7.44 (d, J = 8.8 Hz, 2H), 7.63 (d, J = 8.8 Hz, 2H). | MS ($C_{20}H_{18}BrNO_3$; MWt. 399 and 401): Observed M − 1 = 398 and 400. |
| 4 | 2-{[(4-Bromophenyl)amino]carbonyl}--7-chloro-3,4-dihydronaphthalene-1-carboxylic Acid | Intermediate 18 | ¹HNMR (CD₃OD): δ 2.69 (t, J = 8.4 Hz, 2H), 2.89 (t, J = 8.4 Hz, 2H), 7.24 (d, J = 2.4 Hz, 1H), 7.26 (d, J = 7.8 Hz, 1H), 7.31 (dd, J = 2.4, 7.8 Hz, 1H), 7.49 (d, J = 7.2 Hz, 2H), 7.60 (d, J = 7.2 Hz, 2H). | MS ($C_{18}H_{13}BrClNO_3$; MWt. 405): Observed M − 1 = 404 and 406. |
| 5 | 2-{[(4-Bromophenyl)amino]carbonyl}-5-phenyl-3,4-dihydronaphthalene-1-carboxylic Acid | Intermediate 19 | ¹HNMR (CD₃OD): δ 2.56 (t, J = 7.2 Hz, 2H), 2.82 (t, J = 7.2 Hz, 2H), 7.25-7.49 (m, 8H), 7.49 (d, J = 9.0 Hz, 2H), 7.62 (d, J = 9.0 Hz, 2H) . . . | MS ($C_{24}H_{18}BrNO_3$; MWt. 447): Observed M − 1 = 446 and 448. |
| 6 | 2-{[(4-Bromophenyl)amino]carbonyl}-3,4-dihydronaphthalene-1-carboxylic Acid | 4,5-dihydro-naphto[1,2-c]furan-1,3-dione [CAS 37845-14-0] | ¹HNMR (CD₃OD): δ 2.67 (t, J = 9.0 Hz, 2H), 2.90 (t, J = 9.0 Hz, 2H), 7.15-7.35 (m, 4H), 7.47 (d, J = 9.0 Hz, 2H), 7.60 (d, J = 9.0 Hz, 2H). | MS ($C_{18}H_{14}BrNO_3$; MWt. 371 and 373): Observed M − 1 = 370 and 372. |
| 7 | 2-{[(4-Bromophenyl)amino]carbonyl}-5,7-dimethyl-3,4-dihydronaphthalene-1-carboxylic Acid | Intermediate 20 | ¹HNMR (CD₃OD): δ ppm 2.21 (s, 3H), 2.27 (s, 3H), 2.55-2.65 (m, 2H), 2.70-2.80 (m, 2H), 6.89 (s, 1H), 6.95 (s, 1H), 7.46 (d, J = 7.8 Hz, 2H), 7.61 (d, J = 7.8 Hz, 2H). | MS ($C_{20}H_{18}BrNO_3$; MWt. 399 and 401): Observed M − 1 = 398 and 400. |

TABLE 6-continued

| Comp. No. | IUPAC name Structure | Reagent(s) Reactant(s) | $^1$H NMR δ (ppm) for Compound | Characteristics |
|---|---|---|---|---|
| 8 | 2-{[(4-Bromophenyl)amino]carbonyl}--5,8-dimethyl-3,4-dihydronaphthalene-1-carboxylic Acid | 4,5-dihydro-6,9-dimethyl-naphto[1,2-c]furan-1,3-dione [CAS-24018-47-1] | $^1$H NMR (CD$_3$OD) δ ppm 2.28 (s, 3H), 2.29 (s, 3H), 2.46 (t, J = 6.0 Hz, 2H), 2.78 (t, J = 6.0 Hz, 2H), 6.95 (d, J = 6.0 Hz, 1H), 7.04 (d, J = 6.0 Hz, 1H), 7.46 (d, J = 9.0 Hz, 2H), 7.55 (d, J = 9.0 Hz, 2H). | MS (C$_{20}$H$_{18}$BrNO$_3$; MWt. 399 and 401): Observed M − 1 = 398 and 400. |
| 9 | 3-{[(4-Bromophenyl)amino]carbonyl}-naphthalene-2-carboxylic Acid | naphto[2,,3-c]furan-1,3-dione [CAS 716-39-2] | $^1$H NMR (CD$_3$OD) δ 6.92 (s, 1H), 7.48 (d, J = 9.0 Hz, 2H), 7.66 (d, J = 9.0 Hz, 2H), 7.67 (brs, 2H), 8.02 (s, 1H), 8.03 (s, 1H), 8.07 (s, 1H). | MS (C$_{18}$H$_{12}$BrNO$_3$; MWt. 369 and 371): Observed M − 1 = 368 and 370. |
| 10 | 3-{[(4-Bromophenyl)amino]carbonyl}-5,5,8,8-tetramethyl-5,6,7,8-tetrahydronaphthalene-2-carboxylic Acid | 5,5,8,8-Tetramethyl-5,6,7,8-tetrahydronaphtho[2,3-c]-furan-1,3-dione [CAS 58848-04-7] | $^1$HNMR (CD$_3$COCD$_3$): δ 1.32 (s, 6H), 1.34 (s, 6H), 1.76 (s, 4H), 7.49 (d, J = 8.4 Hz, 2H), 7.56 (s, 1H), 7.77 (d, J = 8.4 Hz, 2H), 7.93 (s, 1H). | MS (C$_{22}$H$_{24}$BrNO$_3$; MWt. 429 and 431): Observed M − 1 = 428 and 430. |
| 11 | 2-{[(4-Bromophenyl)amino]carbonyl}-1-naphthoic Acid | 4,5-dihydro-naphto[1,2-c]furan-1,3-dione [CAS 5343-99-7] | $^1$H NMR (CDCl$_3$): δ 7.40 (d, J = 9.0 Hz, 2H), 7.50-7.70 (m, 4H), 7.80-7.95 (m, 3H), 8.00 (d, J = 9.0 Hz, 1H). | MS (C$_{18}$H$_{12}$BrNO$_3$; MWt. 369 and 371): Observed M − 1 = 368 and 370. |
| 12 | 2-{[(4-Bromophenyl)amino]carbonyl}-4-ethyl-1-naphthoic Acid | Intermediate 22 | $^1$H NMR (CDCl$_3$): δ 1.46 (t, J = 9.0 Hz, 3H), 3.26 (q, J = 9.0 Hz, 2H), 7.75-7.85 (m 3H), 8.15-8.27 (m, 1H), 8.75-8.90 (m, 1H). | MS (C$_{20}$H$_{16}$BrNO$_3$; MWt. 397 and 399): Observed M − 1 = 396 and 398. |

Example 11

Biological Data

Biological activity of compounds according to Formula 1 is set forth in Table 7 below. CHO-Gα16 cells stably expressing FPRL1 were cultured in (F12, 10% FBS, 1% PSA, 400 µg/ml geneticin and 50 µg/ml hygromycin) and HEK-Gqi5 cells stable expressing FPR1 were cultured in (DMEM high glucose, 10% FBS, 1% PSA, 400 µg/ml geneticin and 50 µg/ml hygromycin). In general, the day before the experiment, 18,000 cells/well were plated in a 384-well clear bottom poly-d-lysine coated plate. The following day the screening compound-induced calcium activity was assayed on the FLIPR$^{Tetra}$. The drug plates were prepared in 384-well microplates using the EP3 and the MultiPROBE robotic liquid handling systems. Compounds were tested at concentrations ranging from 0.61 to 10,000 nM. Results are expressed as EC$_{50}$ (nM) and efficacy values.

TABLE 7

| IUPAC name | FPRL-1 Ga16-CHO EC$_{50}$ (eff %) |
|---|---|
| 2-{[(4-bromophenyl)amino]carbonyl}-7-tert-butyl-3,4-dihydronaphthalene-1-carboxylic acid | 1322 nM (86) |
| 2-{[(4-Bromophenyl)amino]carbonyl}-5-isopropyl-3,4-dihydronaphthalene-1-carboxylic acid | 756 nM (80) |
| 2-{[(4-Bromophenyl)amino]carbonyl}-4,4-dimethyl-3,4-dihydronaphthalene-1-carboxylic acid | 87 nM (95) |
| 2-{[(4-bromophenyl)amino]carbonyl}-7-chloro-3,4-dihydronaphthalene-1-carboxylic acid | 777 nM (81) |
| 2-{[(4-bromophenyl)amino]carbonyl}-3,4-dihydronaphthalene-1-carboxylic acid | 383 nM (90) |
| 2-{[(4-bromophenyl)amino]carbonyl}-5,8-dimethyl-3,4-dihydronaphthalene-1-carboxylic acid | 198 nM (93) |
| 2-{[(4-bromophenyl)amino]carbonyl}-5,7-dimethyl-3,4-dihydronaphthalene-1-carboxylic acid | 3922 nM (95) |
| 2-{[(4-bromophenyl)amino]carbonyl}-5-phenyl-3,4-dihydronaphthalene-1-carboxylic acid | 566 nM (100) |
| 2-{[(4-bromophenyl)amino]carbonyl}-1-naphthoic acid | 1295 nM (100) |
| 2-{[(4-bromophenyl)amino]carbonyl}-4-ethyl-naphthalene]-1-carboxylic acid | 165 nM (95) |
| 3-{[(4-bromophenyl)amino]carbonyl}-5,5,8,8-tetramethyl-5,6,7,8-tetrahydronaphthalene-2-carboxylic acid | 1565 nM (58) |
| 3-{[(4-bromophenyl)amino]carbonyl}-2-naphthoic acid | 5928 nM (92) |

What is claimed is:

1. A method of treating a disorder associated with the N-Formyl peptide receptor 2 modulation, wherein the disorder is selected from: ocular inflammatory diseases, wet age-related macular degeneration, dry age-related macular degeneration, corneal wound healing, uveitis, dry eye, Keratitis, allergic eye diseases, conditions affecting the posterior part of the eye, maculopathies, retinal degeneration, non-exudative age related macular degeneration, exudative age related macular degeneration, choroidal neovascularization, diabetic retinopathy, retinopathy of prematurity acute macular neuroretinopathy, central serous chorioretinopathy, cystoid macular edema, diabetic macular edema, infectious keratitis, herpetic keratitis, corneal angiogenesis, lymphangiogenesis, post-surgical corneal inflammation, and blepharitis, which comprises administering to a mammal in need thereof, a pharmaceutical composition comprising a therapeutically effective amount of at least one compound represented by Formula I or a pharmaceutically acceptable salt thereof:

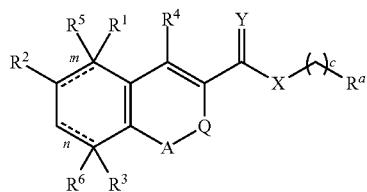

Formula I wherein:

" $\overset{m}{-\!-\!-\!-}$ " is a single bond or a double bond;

" $\overset{n}{-\!-\!-\!-}$ " is a single bond or a double bond;

$R^1$ is H, halogen, —S(O)R$^{10}$, —S(O)$_2$R$^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)R$^{12}$, NR$^{13}$R$^{14}$, C$_{3-8}$ cycloalkyl, C$_{3-8}$ cycloalkenyl or hydroxyl;

$R^2$ is H, halogen, —S(O)R$^{10}$, —S(O)$_2$R$^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)R$^{12}$, NR$^{13}$R$^{14}$, C$_{3-8}$ cycloalkyl, C$_{3-8}$ cycloalkenyl or hydroxyl;

$R^3$ is H, halogen, —S(O)R$^{10}$, —S(O)$_2$R$^{11}$, nitro, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)R$^{12}$, NR$^{13}$R$^{14}$, C$_{3-8}$ cycloalkyl, C$_{3-8}$ cycloalkenyl, C$_{6-10}$ aryl or hydroxyl;

$R^4$ is H or C(O)R$^{12}$;

$R^5$ is H, —OC$_{1-6}$ alkyl, —SC$_{1-6}$ alkyl, —C$_{1-6}$ alkyl, —C$_{2-6}$ alkenyl or —C$_{2-6}$ alkynyl;

$R^6$ is H, —OC$_{1-6}$ alkyl, —SC$_{1-6}$ alkyl, —C$_{1-6}$ alkyl, —C$_{2-6}$ alkenyl or —C$_{2-6}$ alkynyl;

Y is O or S;

X is O, NR, or CH$_2$;

$R^a$ is C$_{6-10}$ aryl,

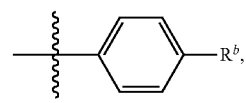

heteroaryl, C$_{3-8}$ cycloalkyl, C$_{3-8}$ cycloalkenyl or H;

$R^b$ is halogen;

c is 0, 1 or 2;

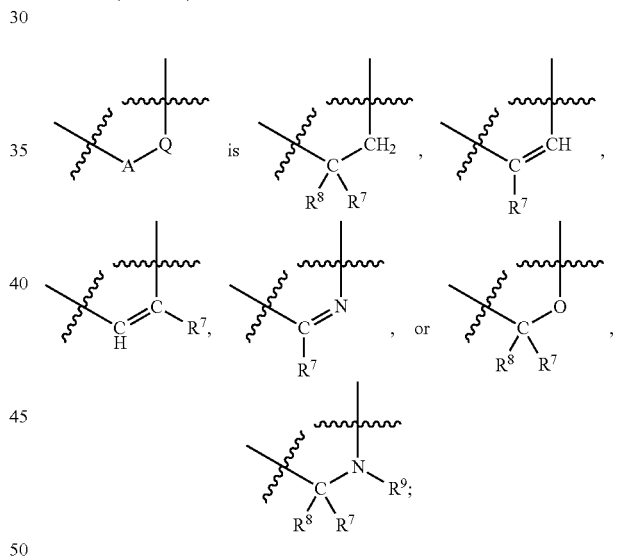

$R^7$ is H, halogen, —S(O)R$^{10}$, —S(O)$_2$R$^{11}$, nitro, hydroxyl, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)R$^{12}$, NR$^{13}$R$^{14}$, C$_{3-8}$ cycloalkenyl or C$_{3-8}$ cycloalkyl;

$R^8$ is H, halogen, —S(O)R$^{10}$, —S(O)$_2$R$^{11}$, cyano, —OC$_{1-6}$ alkyl, —SC$_{1-6}$ alkyl, —C$_{1-6}$ alkyl, —C$_{2-6}$ alkenyl, —C$_{2-6}$ alkynyl, C(O)R$^{12}$, NR$^{13}$R$^{14}$, C$_{3-8}$ cycloalkenyl or C$_{3-8}$ cycloalkyl;

$R^9$ is H, —S(O)$_2$R$^{11}$, —OC$_{1-6}$ alkyl, —SC$_{1-6}$ alkyl, —C$_{1-6}$ alkyl, —C$_{2-6}$ alkenyl, —C$_{2-6}$ alkynyl, C(O)R$^{12}$, C$_{3-8}$ cycloalkenyl or C$_{3-8}$ cycloalkyl;

$R^{10}$ is —C$_{1-6}$ alkyl, C$_{3-8}$ cycloalkyl, or C$_{3-8}$ cycloalkenyl;

$R^{11}$ is H, hydroxyl, —C$_{1-6}$ alkyl, C$_{3-8}$ cycloalkyl or C$_{3-8}$ cycloalkenyl;

$R^{12}$ is H, hydroxyl, —C$_{1-6}$ alkyl, C$_{3-8}$ cycloalkyl, C$_{3-8}$ cycloalkenyl, NR$^{13}$R$^{14}$ or —OC$_{1-6}$ alkyl;

R[13] is H, —C$_{1-6}$ alkyl, C$_{3-8}$ cycloalkyl, C$_{3-8}$ cycloalkenyl SO$_2$R[11] or C(O)R[15];

R[14] is H, —C$_{1-6}$ alkyl, C$_{3-8}$ cycloalkenyl, aryl, heterocycle or C$_{3-8}$ cycloalkyl;

R[15] is H, —C$_{1-6}$ alkyl, C$_{3-8}$ cycloalkenyl or C$_{3-8}$ cycloalkyl; and R is H, —C$_{1-6}$ alkyl, C$_{3-8}$ cycloalkenyl or C$_{3-8}$ cycloalkyl;

with the provisos when "┄┄" is a double bond then R[5] and R[6] are void; and the compound is not of structures

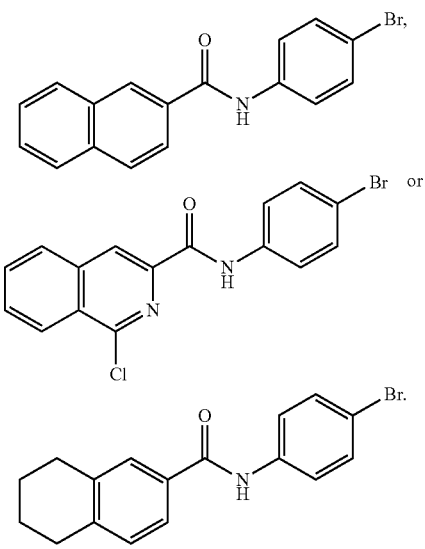

2. The method according to claim 1, wherein said compound is represented by Formula I wherein:

"┄$^m$┄" is a single bond or a double bond;

"┄$^n$┄" is a single bond or a double bond;

R[1] is H, halogen, nitro, cyano, —OC$_{1-6}$ alkyl, —SC$_{1-6}$ alkyl, —C$_{1-6}$ alkyl, C(O)R[12], NR[13]R[14], C$_{3-8}$ cycloalkyl, C$_{3-8}$ cycloalkenyl or hydroxyl;

R[2] is H, halogen, nitro, cyano, —OC$_{1-6}$ alkyl, —SC$_{1-6}$ alkyl, —C$_{1-6}$ alkyl, C(O)R[12], NR[13]R[14], C$_{3-8}$ cycloalkyl, C$_{3-8}$ cycloalkenyl or hydroxyl;

R[3] is H, halogen, nitro, cyano, —OC$_{1-6}$ alkyl, —SC$_{1-6}$ alkyl, —C$_{1-6}$ alkyl, C(O)R[12], NR[13]R[14], C$_{3-8}$ cycloalkyl, C$_{3-8}$ cycloalkenyl, C$_{6-10}$ aryl or hydroxyl;

R[4] is H or C(O)R[12];

R[5] is H, —OC$_{1-6}$ alkyl, —SC$_{1-6}$ alkyl or —C$_{1-6}$ alkyl;

R[6] is H, —OC$_{1-6}$ alkyl, —SC$_{1-6}$ alkyl or —C$_{1-6}$ alkyl;

Y is O;

X is NR;

R$^a$ is

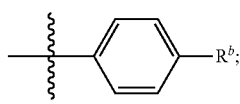

R$^b$ is bromine;

c is 0;

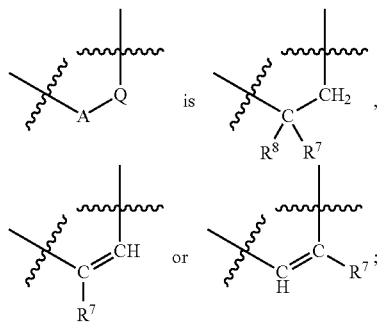

R[7] is H, halogen, nitro, cyano, —SC$_{1-6}$ alkyl, —C$_{1-6}$ alkyl, C(O)R[12], C$_{3-8}$ cycloalkenyl or C$_{3-8}$ cycloalkyl;

R[8] is H, halogen, cyano, —OC$_{1-6}$ alkyl, —SC$_{1-6}$ alkyl, —C$_{1-6}$ alkyl, C(O)R[12], NR[13]R[14], C$_{3-8}$ cycloalkenyl or C$_{3-8}$ cycloalkyl;

R[12] is H, hydroxyl, —C$_{1-6}$ alkyl, C$_{3-8}$ cycloalkyl, C$_{3-8}$ cycloalkenyl, NR[13]R[14] or —OC$_{1-6}$ alkyl;

R[13] is H, —C$_{1-6}$ alkyl, C$_{3-8}$ cycloalkyl, C$_{3-8}$ cycloalkenyl or C(O)R[15];

R[14] is H, —C$_{1-6}$ alkyl, C$_{3-8}$ cycloalkenyl, aryl, heterocycle or C$_{3-8}$ cycloalkyl;

R[15] is H, —C$_{1-6}$ alkyl, C$_{3-8}$ cycloalkenyl or C$_{3-8}$ cycloalkyl; and R is H;

with the provisos:

when "┄┄" is a double bond then R[5] and R[6] are void; and the compound is not of structures

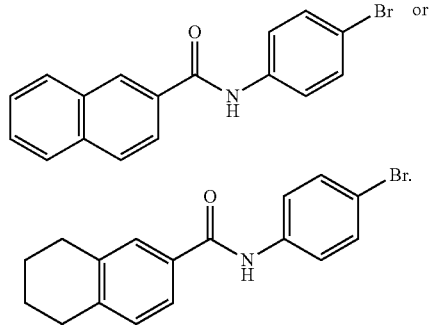

3. The method according to claim 1, wherein said compound is represented by Formula I wherein:

"┄$^m$┄" is a double bond;

"┄$^n$┄" is a double bond;

R[1] is H or —C$_{1-6}$ alkyl;

R[2] is H, halogen or —C$_{1-6}$ alkyl;

R[3] is H, C$_{6-10}$ aryl or —C$_{1-6}$ alkyl;

R[4] is C(O)R[12];

Y is O;

X is NR;

R$^a$ is

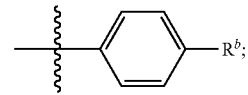

$R^b$ is bromine;
c is 0;

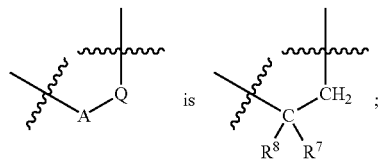 ;

$R^7$ is H or $C_{1-6}$ alkyl;
$R^8$ is H or —$C_{1-6}$ alkyl;
$R^{12}$ is hydroxyl; and
R is H.

4. The method according to claim 1, wherein said compound is represented by Formula I wherein:

" $\overset{m}{\text{-----}}$ " is a double bond;

" $\overset{n}{\text{-----}}$ " is a double bond;

$R^1$ is H;
$R^2$ is H;
$R^3$ is H;
$R^4$ is H or $C(O)R^{12}$;
Y is O;
X is NR;
$R^a$ is

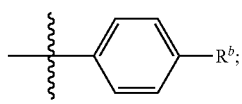

$R^b$ is bromine;
c is 0;

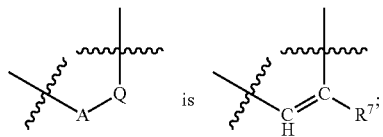

$R^7$ is H or $C(O)R^{12}$;
$R^{12}$ is hydroxyl;
R is H; and
the compound is not of structure

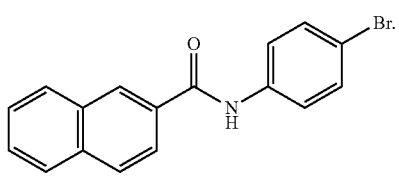 [SMILES: O=C(Nc1ccc(Br)cc1)c1ccc2ccccc2c1]

5. The method according to claim 1, wherein said compound is represented by Formula I wherein:

" $\overset{m}{\text{-----}}$ " is a double bond;

" $\overset{n}{\text{-----}}$ " is a double bond;

$R^1$ is H;
$R^2$ is H;
$R^3$ is H;

$R^4$ is $C(O)R^{12}$;
Y is O;
X is NR;
$R^a$ is

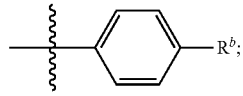

$R^b$ is bromine;
c is 0;

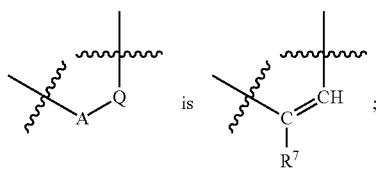

$R^7$ is $C_{1-6}$ alkyl;
$R^{12}$ is hydroxyl; and
R is H.

6. The method according to claim 1, wherein said compound is represented by Formula I wherein:

" $\overset{m}{\text{-----}}$ " is a single bond;

" $\overset{n}{\text{-----}}$ " is a single bond;

$R^1$ is —$C_{1-6}$ alkyl;
$R^2$ is H;
$R^3$ is —$C_{1-6}$ alkyl;
$R^4$ is $C(O)R^{12}$;
$R^5$ is, —$C_{1-6}$ alkyl;
$R^6$ is, —$C_{1-6}$ alkyl;
Y is O;
X is NR;
$R^a$ is

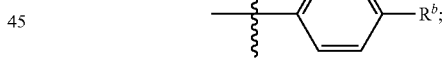

$R^b$ is bromine;
c is 0;

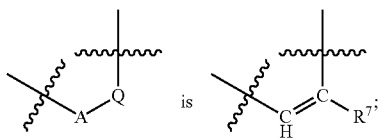

$R^7$ is $C(O)R^{12}$;
$R^{12}$ is hydroxyl; and
R is H.

7. The method according to claim 1, wherein said compound represented by Formula I is selected from:

2-{[(4-Bromophenyl)amino]carbonyl}-7-tert-butyl-3,4-dihydronaphthalene-1-carboxylic acid;

2-{[(4-Bromophenyl)amino]carbonyl}-5-isopropyl-3,4-dihydronaphthalene-1-carboxylic acid;

2-{[(4-Bromophenyl)amino]carbonyl}-4,4-dimethyl-3,4-dihydronaphthalene-1-carboxylic acid;
2-{[(4-Bromophenyl)amino]carbonyl}-7-chloro-3,4-dihydronaphthalene-1-carboxylic acid;
2-{[(4-Bromophenyl)amino]carbonyl}-3,4-dihydronaphthalene-1-carboxylic acid;
2-{[(4-Bromophenyl)amino]carbonyl}-5,8-dimethyl-3,4-dihydronaphthalene-1-carboxylic acid;
2-{[(4-Bromophenyl)amino]carbonyl}-5,7-dimethyl-3,4-dihydronaphthalene-1-carboxylic acid;
2-{[(4-Bromophenyl)amino]carbonyl}-5-phenyl-3,4-dihydronaphthalene-1-carboxylic acid;
2-{[(4-Bromophenyl)amino]carbonyl}-1-naphthoic acid;
2-{[(4-Bromophenyl)amino]carbonyl}-4-ethyl-1-naphthoic acid;
3-{[(4-Bromophenyl)amino]carbonyl}-5,5,8,8-tetramethyl-5,6,7,8-tetrahydronaphthalene-2-carboxylic acid; and
3-{[(4-Bromophenyl)amino]carbonyl}-2-naphthoic acid.

8. The method according to claim 1, wherein said mammal is a human.

* * * * *